(12) United States Patent
Kambayashi

(10) Patent No.: US 10,980,820 B2
(45) Date of Patent: Apr. 20, 2021

(54) COMPOSITIONS AND METHODS FOR SUPPRESSING OR REDUCING SYSTEMIC IMMUNE RESPONSE IN A SUBJECT

(71) Applicant: THE TRUSTEES OF THE UNIVERSITY OF PENNSYLVANIA, Philadelphia, PA (US)

(72) Inventor: Taku Kambayashi, Malvern, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 16/509,065

(22) Filed: Jul. 11, 2019

(65) Prior Publication Data
US 2020/0101088 A1 Apr. 2, 2020

Related U.S. Application Data

(63) Continuation of application No. 15/558,347, filed as application No. PCT/US2016/022661 on Mar. 16, 2016, now Pat. No. 10,391,107.

(60) Provisional application No. 62/133,665, filed on Mar. 16, 2015.

(51) Int. Cl.
| A61K 31/593 | (2006.01) |
| A61K 45/06 | (2006.01) |
| A61K 38/32 | (2006.01) |

(52) U.S. Cl.
CPC ............ *A61K 31/593* (2013.01); *A61K 45/06* (2013.01); *A61K 38/32* (2013.01)

(58) Field of Classification Search
None
See application file for complete search history.

(56) References Cited

U.S. PATENT DOCUMENTS

| 5,190,935 A | 3/1993 | Binderup et al. |
| 2002/0103172 A1 | 8/2002 | Von Daehne |
| 2003/0175333 A1 | 9/2003 | Shefer et al. |
| 2004/0058895 A1 | 3/2004 | Mazess et al. |
| 2010/0087406 A1 | 4/2010 | Gombart et al. |
| 2010/0196308 A1 | 8/2010 | Jimenez et al. |
| 2011/0123502 A1* | 5/2011 | Barry .................. C12N 5/0636 424/93.71 |
| 2013/0095155 A1 | 4/2013 | McHale et al. |

FOREIGN PATENT DOCUMENTS

| EP | 1891944 A1 | 2/2008 |
| WO | 2008157394 A2 | 12/2008 |
| WO | 2014162007 A2 | 10/2014 |

OTHER PUBLICATIONS

Toomer and Malek, "Cytokine signaling in the development and homeostasis of regulatory T cells", Cold Spring Harb Perspect Biol, 1-17, 10:a028597 (2018) (Year: 2018).*
Zhong et al.,"TSLP signaling pathway map: a platform for analysis of TSLP-mediated signaling", Database, vol. 2014, article ID bau007; doi: 10.1093/database/bau007. (Year: 2014).*
Encyclopedia Britannica, Drug, accessed May 18, 2018, Encyclopedia Britannica, pp. 1-23 (year: 2018).
International Search Report and Written Opinion for PCT International Application No. PCT/US2016/022661 dated Sep. 1, 2016.
Bouillon, et al., Vitamin D analogs with low affinity for the vitamin D binding protein: enhanced in vitro and decreased in vivo activity, J Bone Miner Res. 6(10) ,1991 ,1051-1057 (abstract only).
Brown, et al., Vitamin D analogs: therapeutic applications and mechanisms for selectivity, Mol Aspects Med. 29(6) ,2008 ,433-452.
Elstner, et al., 20-epi-vitamin D3 analogues: a novel class of potent inhibitors of proliferation and inducers of differentiation of human breast cancer cell lines, Cancer Res. 55(13) ,Jul. 1995 ,2822-2830.
Ghoreishi, et al., Expansion of Antigen-Specific Regulatory T Cells with the Topical Vitamin D Analog Calcipotriol, J Immunol. 82(10) ,May 2009 ,6071-6078.
Posner, et al., Conceptually new 20-epi-22-oxa sulfone analogues of the hormone 1alpha,25-dihydroxyvitamin D(3): synthesis and biological evaluation, J Med Chem. 43(19) ,Sep. 2000 ,3581-3586.

* cited by examiner

*Primary Examiner* — Anand U Desai
(74) *Attorney, Agent, or Firm* — Saul Ewing Arnstein & Lehr LLP; Kathryn Doyle; Domingos J. Silva

(57) ABSTRACT

The present invention includes a method of suppressing systemic immune response in a subject, the method comprising topically administering a pharmaceutically effective amount of a vitamin D analog to a subject in need thereof. The present invention further includes a method of treating an autoimmune disease in a subject, the method comprising topically administering a pharmaceutically effective amount of a vitamin D analog to a subject in need thereof.

6 Claims, 13 Drawing Sheets

Specification includes a Sequence Listing.

COMPOSITIONS AND METHODS FOR SUPPRESSING OR REDUCING SYSTEMIC IMMUNE RESPONSE IN A SUBJECT

CROSS REFERENCE TO RELATED APPLICATIONS

The present application is a continuation of, and claims priority to, U.S. patent application Ser. No. 15/558,347 filed Sep. 14, 2017, now U.S. Pat. No. 10,391,107, which is a 35 U.S.C. § 371 national phase application from, and claims priority to, International Application No. PCT/US2016/022661, filed Mar. 16, 2016, and published under PCT Article 21(2) in English, which claims priority to U.S. Provisional Application No. 62/133,665, filed Mar. 16, 2015, the contents of all of which are incorporated by reference herein in their entireties.

STATEMENT REGARDING FEDERALLY SPONSORED RESEARCH OR DEVELOPMENT

This invention was made with government support under grant number R01HL111501 awarded by National Institutes of Health. The government has certain rights in the invention.

BACKGROUND OF THE INVENTION

In order to suppress or reduce immune responses in inflammatory diseases, immunomodulatory drugs often need to be administered systemically, so that they can reach the lymphoid organs at the effective concentrations that are required to modulate the immune response. This results in systemic spread of the immunomodulatory drug throughout the body, causing unwanted off-target side effects. Moreover, most of these drugs have to be administered by intravenous injection, which is burdensome for patients and carry additional risks such as infusion reactions and infections. Administration of immunomodulatory drugs through the skin or by inhalation has been restricted to treatment of localized autoimmune or hypersensitivity reactions that affect the skin or the airways (e.g., psoriasis or asthma, respectively).

Epidemiological studies have associated vitamin D deficiency with a variety of diseases including type I diabetes (T1D). The impact of vitamin D deficiency on immune cells has been thought to be direct, with studies showing that vitamin D can directly suppress the activation of immune cells such as T cells, dendritic cells, monocytes/macrophages, and B cells. However, clinical trials to investigate the effects of oral or intravenous vitamin D supplementation in patients have been met with limited success. The effects of vitamin D supplementation was ineffective or modest at best, because the doses of vitamin D that need to be administered systemically for therapeutic effect cause serious side effects such as hypercalcemia.

There is thus a need in the art to develop novel methods of suppressing systemic immune responses in a subject. Such methods should be useful in treating systemic inflammatory diseases and avoid serious side effects associated with the drug's systemic exposure. The present invention fulfills this need.

BRIEF SUMMARY OF THE INVENTION

The invention provides a method of increasing systemic regulatory T cell (Treg) levels in a subject in need thereof. The invention further provides a method of suppressing or reducing systemic immune response in a subject in need thereof. The invention further provides a method of treating a systemic inflammatory disease or disorder in a subject in need thereof, wherein the disease or disorder is selected from the group consisting of type I diabetes, type II diabetes, atherosclerosis, multiple sclerosis, and rheumatoid arthritis. The invention further provides a kit for suppressing or reducing systemic immune response in a subject.

In certain embodiments, the method comprises topically administering to the subject a pharmaceutically effective amount of a vitamin $D_3$ analog. In other embodiments, the analog is the only biologically active agent administered to the subject. In yet other embodiments, the analog is the only biologically active agent administered to the subject in an amount sufficient to increase systemic regulatory T cell (Treg) levels in the subject. In other embodiments, the systemic Treg levels in the subject are at least about 20% higher than the systemic Treg levels in a control subject.

In certain embodiments, administration of the analog increases systemic regulatory T cell (Treg) levels in the subject.

In certain embodiments, the subject is afflicted with an inflammatory disease. In other embodiments, the subject is afflicted with at least one disease or disorder selected from the group consisting of type I diabetes, type II diabetes, atherosclerosis, multiple sclerosis and rheumatoid arthritis.

In certain embodiments, the analog has lower calcemic activity than 1,25-dihydrovitamin $D_3$. In other embodiments, the analog is selected from the group consisting of $1\alpha,18,25\text{-(OH)}_3 D_3$; 23-(m-(Dimethylhydroxymethyl)-22-yne-24,25,26,27(tetranor)-1α-OH)$_2 D_3$; 1α,25-Dihydroxy-trans-Isotachysterol (1,25-trans-Iso-T); (1S,3R,6S)-7,19-Retro-1,25-(OH)$_2 D_3$; (1S,3R,6R)-7,19-Retro-1,25-(OH)$_2 D_3$; 22-(p-(Hydroxyphenyl)-23,24,25,26,27-pentanor-$D_3$; 22-(m-(Hydroxyphenyl)-23,24,25,26,27-pentanor-$D_3$; 26,27-cyclo-22-ene-1α,24S-dihydroxyvitamin $D_3$ (MC903 or calcipotriol); 1(S),3(R)-dihydroxy-20(R)-(5'-ethyl-5'-hydroxy-hepta-1'(E),3'(E)-dien-1'-yl)-9,10-seco-pregna-5(Z),7(E),10(19)-triene (EB1089); 1α,25-(OH)-20-epi-22-oxa-24,26,27-trishomovitamin D (KH1060); 22-oxa-1α,25(OH)$_2 D_3$ (OCT or 22-OXA); 1R,25-dihydroxy-21-(3-hydroxy-3-methylbutyl)vitamin $D_3$; and any combinations thereof. In yet other embodiments, the analog is selected from the group consisting of MC903, EB1089, 22-OXA, and any combinations thereof. In yet other embodiments, the vitamin $D_3$ analog is MC903.

In certain embodiments, the subject is a mammal. In other embodiments, the mammal is human.

In certain embodiments, the analog is administered topically to the subject in a dosing schedule wherein a treatment week is followed by a no-treatment week. In other embodiments, in the treatment week, the subject is topically administered the analog at a frequency selected from the group consisting of: every day and every other day. In yet other embodiments, the analog is applied to a given skin area of the subject, such that about 0.2 nmol to about 20 nmol analog per $cm^2$ of given skin are administered to the subject. In yet other embodiments, the given skin area in the subject ranges from about 100 $cm^2$ to 2,500 $cm^2$. In yet other embodiments, wherein the analog is formulated in a pharmaceutical composition comprising between about 0.005% and about 10% (w/w) of the analog. In yet other embodiments, the pharmaceutical composition comprise no additional agent, besides the analog, that increases systemic regulatory T cell (Treg) levels in the subject.

In certain embodiments, the method comprises administering to the subject a pharmaceutically effective amount of a polypeptide comprising a thymic stromal lymphopoietin (TSLP) isoform. In other embodiments, the isoform has at least 85%, 90%, 95% or 99% identity with at least one selected from the group consisting of SEQ ID NO:1 and SEQ ID NO:2. In yet other embodiments, the TSLP isoform is at least one selected from the group consisting of SEQ ID NO:1 and SEQ ID NO:2. In yet other embodiments, the polypeptide is administered by at least one route selected from the group consisting of oral, nasal, inhalational, topical, buccal, rectal, pleural, peritoneal, parenteral (such as subcutaneous, intravenous, intramuscular, intrasternal injection, or infusion), vaginal, transdermal, epidural, intratracheal, otic, intraocular, and intrathecal routes. In yet other embodiments, the polypeptide is the only biologically active agent administered to the subject. In yet other embodiments, the polypeptide is the only biologically active agent administered to the subject in an amount sufficient to increase systemic regulatory T cell (Treg) levels in the subject.

In certain embodiments, the kit comprises at least one agent selected from a vitamin $D_3$ analog and a polypeptide comprising a TSLP isoform, and instructions for administering the agent to the subject. In other embodiments, the analog is to be administered topically to the subject.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1A, comprising FACS data and a graph, illustrates the percentage of regulatory T cells (Tregs) in the ear skin homogenate of B6 mice. "Treated" refers to topical administration of MC903 to the ear skin of the B6 mice. "Untreated" refers to topical administration of EtOH to the ear skin of the B6 mice. FIG. 1B comprises graphs illustrating the percentage of Tregs out of CD4+ T cells in the blood, spleen, and peripheral lymph nodes of B6 mice topically treated with MC903.

FIG. 3A is a graph illustrating the percentage of Tregs out of CD4+ T cells in the spleen and blood of B6 mice over 18 days. FIG. 3B illustrates the absolute numbers of Tregs in the spleen of B6 mice over 18 days. FIG. 3C illustrates the serum thymic stromal lymphopoietin (TSLP) level change over time in B6 mice over 18 days.

FIG. 4A illustrates Bromodeoxyuridine (BrdU) incorporation in Tregs on Day 8 in the spleen of B6 mice. FIG. 4B illustrates BrdU incorporation in conventional T cells (Tconvs) on Day 8 in the spleen of B6 mice.

FIG. 5A illustrates the percentage of Tregs out of CD4+ T cells in the blood of NOD mice before (Day 0) and after treatment (Day 8). FIG. 5B illustrates the percentage of mice exhibiting diabetes (two consecutive days of blood glucose level>250 mg/dL) from each group. The % of mice with diabetes is plotted over the age of the mice (N=7 mice/group-EtOH; N=8 mice/group-MC903).

FIG. 6A illustrates the total cholesterol levels at baseline, at week 3, and week 10 of ApoE KO mice. FIG. 6B illustrates the atherosclerotic plaques difference among ApoE KO mice. The full length of the aorta was removed from the mice at week 10 and stained with Oil Red 0 dye to detect atherosclerotic plaques. The area occupied by the plaque was calculated and divided by the total area of the aorta (% lesion area). N=7 mice/group. * indicates significance of $p<0.01$ by T-test.

FIG. 8A illustrates the percentage of Tregs in blood of B6 mice determined on Day 8 post MC903 treatment in comparison with EtOH treatment. FIG. 8B illustrates the change of ankle thickness over time after B6 mice were injected with 75 µl of serum from K/B×N mice on Days 0 and 2, and were topically treated with MC903 starting at Day 0. Ankle thickness was measured twice a week and plotted as % maximal ankle thickness of each mouse. N=3 mice/group.

FIG. 9A: MC903, EB1089, and 22-OXA dose at 2 nmol/ear. FIG. 9B: MC903 dose at 2 nmol/ear; EB1089 and 22-OXA dose at 0.4 nmol/ear. FIG. 9C: EB1089 dose at 0.04 nmol/ear. Plasma TSLP was measured by ELISA. N=3 mice/group.

DETAILED DESCRIPTION OF THE INVENTION

Figure 1A:
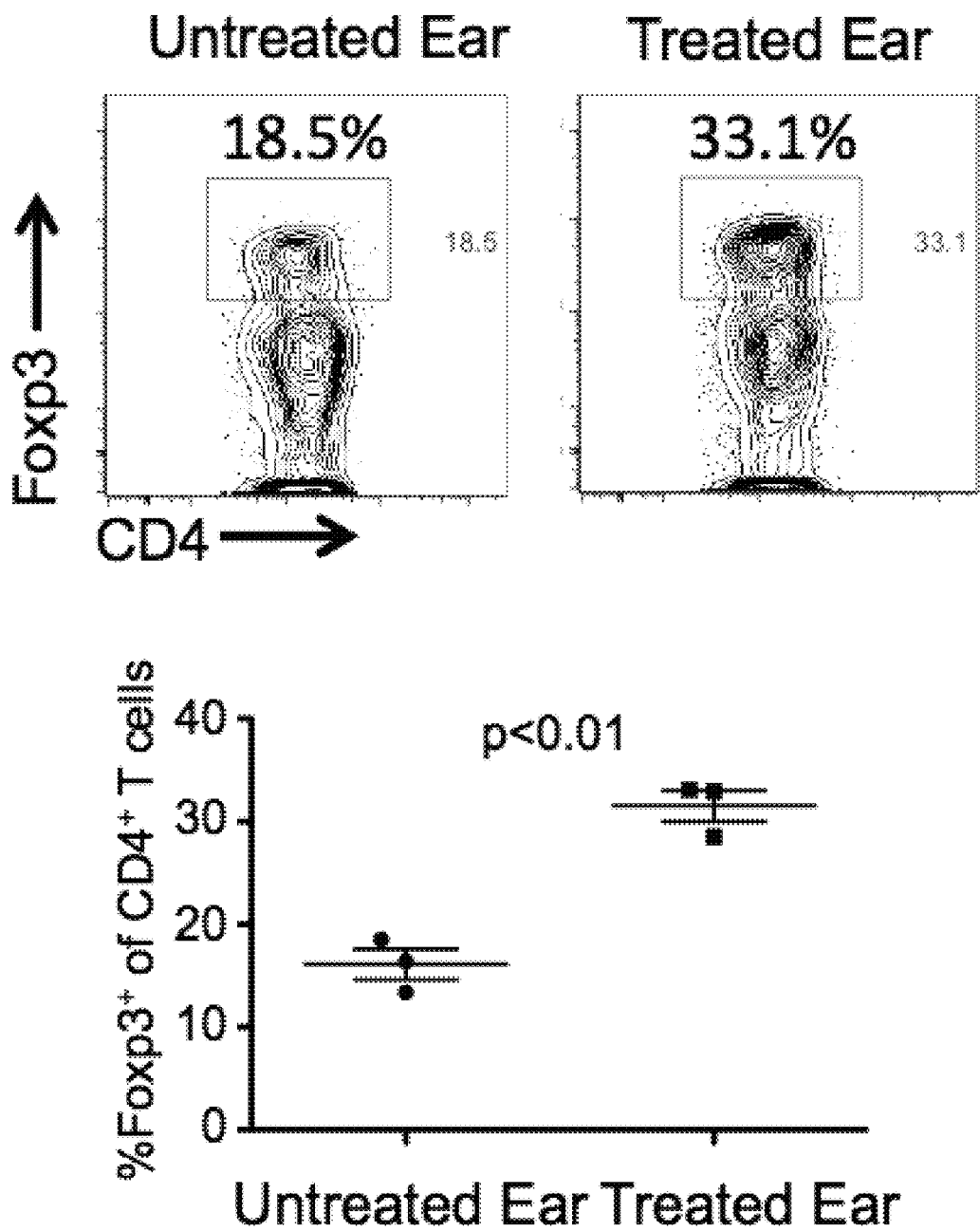
FIGS. 1A-1B comprise graphs relating to topical treatment of B6 mice with EtOH or MC903 (2 nmol) on one ear.

The present invention relates, in one aspect, to the unexpected discovery that topical, but not systemic, administration of a vitamin $D_3$ analog to a subject suppresses or reduces systemic immune response in the subject. In certain embodiments, topical administration of the analog increases systemic regulatory T cells (Tregs) in the subject. Such increase in Treg levels can be observed, for example, in the skin, blood and secondary lymphoid organs (lymph nodes and spleen) of the subject.

In certain embodiments, systemic vitamin $D_3$ analog exposure is not required to achieve systemic immunomodulation. Rather, retention of the vitamin $D_3$ analog in the skin to activate keratinocytes accomplishes the desired immunomodulatory effect without toxicities associated with systemic vitamin $D_3$ exposure. In other embodiments, the analog does not cause significant hypercalcemia (i.e., have low or negligible calcemic activity). In yet other embodiments, the analog causes less hypercalcemia than 1,25-dihydrovitamin $D_3$ (also known as 1,25$(OH)_2D_3$) when administered using the same route at the same dose. In yet other embodiments, the analog has low or negligible skin penetration. In yet other embodiments, the analog has low or negligible binding to vitamin D binding protein, as compared to 1,25-dihydrovitamin $D_3$.

The invention should not be construed to be limited to vitamin $D_3$ analogs, and further encompasses any vitamin D analog known in the art and useful within the methods described herein.

In another aspect, the invention includes methods of treating inflammatory diseases or disorders in a subject, the method comprising topically administering a pharmaceutically effective amount of a composition of the invention to the subject in need thereof.

Definitions

As used herein, each of the following terms have the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics and chemistry are those well-known and commonly employed in the art.

As used herein, the articles "a" and "an" refer to one or to more than one (i.e., to at least one) of the grammatical object of the article. By way of example, "an element" means one element or more than one element.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, ±5%, ±1%, or ±0.1% from the specified value, as such variations are appropriate to perform the disclosed methods.

The term "inflammatory disease" as used herein is defined as a disorder that results from an excessive inflammatory response (or inflammatory overresponse). An inflammatory disease is the result of an inappropriate and excessive response to an inappropriate antigen. Examples of inflammatory diseases include but are not limited to, Addison's disease, alopecia greata, ankylosing spondylitis, autoimmune hepatitis, atherosclerosis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, and ulcerative colitis, among others.

A "disease" is a state of health of an animal wherein the animal cannot maintain homeostasis, and wherein if the disease is not ameliorated, the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the terms "effective amount" or "therapeutically effective amount" or "pharmaceutically effective amount" of a compound are used interchangeably to refer to the amount of the compound sufficient to provide a beneficial effect to the subject to which the compound is administered. The term to "treat," as used herein, means reducing the frequency with which symptoms are experienced by a patient or subject or administering an agent or compound to reduce the severity with which symptoms are experienced. An appropriate therapeutic amount in any individual case may be determined by one of ordinary skill in the art using routine experimentation.

The term "enhancing an immune response" refers to evoking and/or enhancing any response of the animal's immune system, including a cell-mediated (i.e., cytotoxic T lymphocyte mediated) response. These immune responses can be assessed by number of in vitro or in vivo assays well known to those skilled in the art including, but not limited to, immune cell expansion/proliferation, cytotoxic T lymphocyte assays, production of cytokines, regression of tumors, survival of tumor bearing animals, rejection of allografts, graft versus host disease, clearance of pathogens from animals, induction of autoimmune disease in animals, and antibody assays.

As used herein, the term "HFD" refers to high fat diet.

By the term "immune reaction," as used herein, is meant the detectable result of stimulating and/or activating an immune cell.

As used herein, the term "immunomodulation" encompasses all therapeutic interventions aimed at modifying the immune response. Augmentation of the immune response is desirable to, for example, prevent infection in states of immunodeficiency, to fight established infections and to fight cancer.

As used herein, an "instructional material" includes a publication, a recording, a diagram, or any other medium of expression that can be used to communicate the usefulness of a compound, composition, assay or method of the invention in a kit for suppressing or reducing systemic immune response in a subject. The instructional material of the kit of the invention can, for example, be affixed to a container that contains the identified compound, composition, assay, or methods of the invention or be shipped together with a container that contains the identified compound, composition, assay, or method. Alternatively, the instructional material can be shipped separately from the container with the intention that the instructional material and the compound, composition, assay, or method be used cooperatively by the recipient.

"Parenteral" administration of a composition includes, e.g., subcutaneous (s.c.), intravenous (i.v.), intramuscular (i.m.), or intrasternal injection, or infusion techniques.

As used herein, the term "pharmaceutically acceptable" refers to a material, such as a carrier or diluent, which does not abrogate the biological activity or properties of the composition, and is relatively non-toxic, i.e., the material may be administered to an individual without causing undesirable biological effects or interacting in a deleterious manner with any of the components of the composition in which it is contained.

As used herein, the term "pharmaceutical composition" or "composition" refers to a mixture of at least one compound useful within the invention with other chemical components, such as carriers, stabilizers, diluents, dispersing agents, suspending agents, thickening agents, and/or excipients. The pharmaceutical composition facilitates administration of the compound to an organism. Multiple techniques of administering a compound exist in the art including, but not limited to: oral, nasal, inhalational, topical, buccal, rectal, pleural, peritoneal, parenteral (such as subcutaneous (s.c.), intravenous (i.v.), intramuscular (i.m.), intrasternal injection, or infusion), vaginal, transdermal, epidural, intratracheal, otic, intraocular, and intrathecal routes. In certain embodiments, the administration comprises topical administration.

As used herein, a "subject" refers to a human or non-human mammal. Non-human mammals include, for example, livestock and pets, such as ovine, bovine, porcine, canine, feline and murine mammals. In certain embodiments, the subject is human.

As used herein, "topical administration" or "topical application" refers to a medication applied to body surfaces such as the skin or mucous membranes.

As used herein, the term "treatment" or "treating" is defined as the application or administration of a therapeutic agent, i.e., a composition useful within the invention (alone or in combination with another pharmaceutical agent), to a subject, or application or administration of a therapeutic agent to an isolated tissue or cell line from a subject (e.g., for diagnosis or ex vivo applications), who has a disease or disorder, a symptom of a disease or disorder or the potential to develop a disease or disorder, with the purpose to cure, heal, alleviate, relieve, alter, remedy, ameliorate, improve or affect the disease or disorder, the symptoms of the disease or disorder or the potential to develop the disease or disorder. Such treatments may be specifically tailored or modified, based on knowledge obtained from the field of pharmacogenomics.

As used herein, the term "TSLP" refers to thymic stromal lymphopoeitin.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Disclosure

In one aspect, the present invention relates to the unexpected discovery that topical, and not systemic, administration to a subject of at least one vitamin $D_3$ analog (which is optionally part of a composition formulated for topical administration) suppresses or reduces systemic immune response in the subject. In certain embodiments, topical administration of the analog increases systemic regulatory T cells (Tregs) in the subject. Such increase in Treg levels can be observed, for example, in the skin, blood and secondary lymphoid organs (lymph nodes and spleen) of the subject.

Figure 1B:
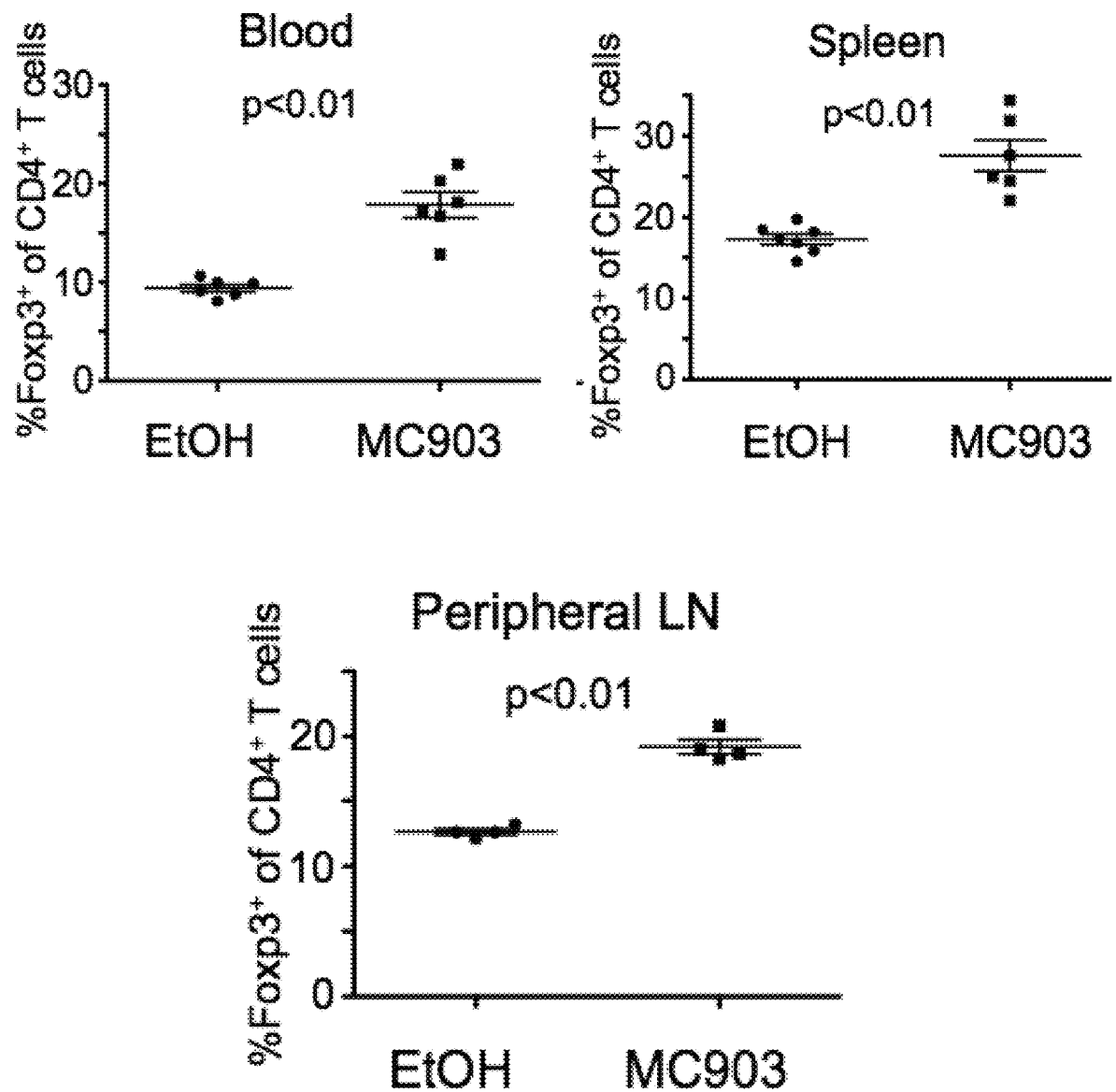

As demonstrated at least in FIGS. 1A-1B, topical administration of a composition comprising a vitamin D analog to a subject increases systemic regulatory T cells (Tregs). The regulatory T cells modulate the immune system in the subject, maintaining tolerance to antigens, and abrogate inflammatory disease. Without wishing to be limited by any theory, this is a "self-check" built into the immune system to prevent excessive reaction.

In certain embodiments, administration of the analog to the skin of the subject increases Treg levels, for example, in the skin, blood and/or secondary lymphoid organs (lymph nodes and spleen) of the subject. In other embodiments, the increase in Treg levels is in the range from about 10%, about 25%, about 50%, about 100%, about 200%, or about 400% as compared to a control. The control may be a similarly situated subject that is topically treated with a placebo, not treated with any medication at all, or treated with a vitamin $D_3$ analog using a route other than topical administration. Alternatively, the control may be the subject when it is not topically treated with a vitamin $D_3$ analog contemplated within the invention.

In certain embodiments, the analog is administered to the skin of the subject. In other embodiments, the analog is administered at least once a day to the subject. In yet other embodiments, the analog is administered once a day to the subject, every other day to the subject, every third day to the subject, and so forth.

In certain embodiments, dosing schedule of the analog for the treatment of inflammatory disease comprises weekly treatment (every day or every other day; minimum of 3 days/week) with at least a week of no treatment, which can be cycled as a dosing schedule.

In certain embodiments, the dose of the analog ranges from about 0.2 nmol to about 20 nmol per $cm^2$ of skin treated. In yet other embodiments, the skin area treated ranges from about 100 $cm^2$ to 2,500 $cm^2$.

In certain embodiments, the subject is a mammal. In other embodiments, the mammal is human.

In another aspect, the invention includes a method of treating type I or type II diabetes, atherosclerosis, multiple sclerosis, or rheumatoid arthritis in a subject in need thereof, the method comprising topically administering a pharmaceutically effective amount of a vitamin $D_3$ analog to the subject.

In certain embodiments, the methods of the present invention can be used to treat inflammatory diseases, which include but are not limited to rheumatoid arthritis, systemic lupus erythematosus, atherosclerosis, dermatomyositis, Still's disease, mixed connective tissue disorders, Sjogren's disease, Behcet's disease, CREST syndrome, immune-mediated thrombocytopenia, inflammatory bowel disease, multiple sclerosis, type 1 and type 2 diabetes (T1D, T2D), Guillain-Barre syndrome, acute and chronic graft-versus-host disease (GVHD), transplant rejection, psoriasis, Graves' disease, autoimmune hepatitis, macrophage-activation syndrome, cytokine-release syndrome, Hashimoto's thyroiditis, Myasthenia gravis, atherosclerosis, and vasculitides.

In certain embodiments, the vitamin $D_3$ analog is at least one selected from the group consisting of:
1α,18,25-$(OH)_3D_3$;
23-(m-(Dimethylhydroxymethyl)-22-yne-24,25,26,27(tetranor)-1α-$OH)_2D_3$;
1α,25-Dihydroxy-trans-Isotachysterol (also known as 1,25-trans-Iso-T);
(1S,3R,6S)-7,19-Retro-1,25-$(OH)_2D_3$;
(1S,3R,6R)-7,19-Retro-1,25-$(OH)_2D_3$;
22-(p-(Hydroxyphenyl)-23,24,25,26,27-pentanor-$D_3$;
22-(m-(Hydroxyphenyl)-23,24,25,26,27-pentanor-$D_3$;
26,27-cyclo-22-ene-1α,24S-dihydroxyvitamin $D_3$ (also known as MC903 or calcipotriol);
1(S),3(R)-dihydroxy-20(R)-(5'-ethyl-5'-hydroxy-hepta-1'(E),3'(E)-dien-1'-yl)-9,10-secopregna-5(Z),7(E),10(19)-triene (also known as EB1089);
1α,25-(OH)-20-epi-22-oxa-24,26,27-trishomovitamin D (also known as KH1060);
22-oxa-1α,25$(OH)_2D_3$ (also known as OCT or 22-OXA);
1R,25-dihydroxy-21-(3-hydroxy-3-methylbutyl)vitamin $D_3$;
and any combinations thereof.

In certain embodiments, the vitamin D analog is MC903.

In another aspect, the present invention relates to the unexpected discovery that administration to a subject of a therapeutically effective amount of a polypeptide comprising a TSLP isoform suppresses or reduces systemic immune response in the subject.

In certain embodiments, the invention includes a method of treating type I or type II diabetes, atherosclerosis, multiple sclerosis, or rheumatoid arthritis in a subject in need thereof, comprising administering to the subject a therapeutically effective amount of a polypeptide comprising a TSLP isoform.

In certain embodiments, the subject is human and the TSLP isoform has at least 85% identity, at least 90% identity, at least 95% identity, or at least 99% identity with at least one selected from the group consisting of SEQ ID NO:1 (MFPFALLYVL SVSFRKIFIL QLVGLVLTYD FTNCDFEKIK AAYLSTISKD LITYMSGTKS TEFNNTVSCS NRPHCLTEIQ SLTFNPTAGC ASLAKEMFAM KTKAALAIWC PGYSETQINA TQAMKKRRKR KVTTNKCLEQ VSQLQGLWRR FNRPLLKQQ) and SEQ ID NO:2 (MFAMKTKAAL AIWCPGYSET QINATQAMKK RRKRKVTTNK CLEQVSQLQG LWRRFNRPLL KQQ). In other embodiments, the subject is human and the TSLP isoform is at least one selected from the group consisting of SEQ ID NO:1 and SEQ ID NO:2. In yet other embodiments, administration of the polypeptide increases systemic regulatory T cells (Tregs) in the subject.

The present invention also pertains to kits useful in any of the methods of the invention described herein. Such kits comprise components useful in any of the methods described herein, including for example, compositions and methods for suppressing or reducing systemic immune response and/or treating inflammatory diseases or disorders in a subject, one or more containers (e.g., test tube, cell culture dish, cell culture plate, cell culture flask, cell culture bag) for containing a component of any of the embodiments of the invention described elsewhere herein, and instructional materials.

Formulations/Administration

The relative amounts of the active ingredient, the pharmaceutically acceptable carrier, and any additional ingredients in a pharmaceutical composition of the invention will vary, depending upon the identity, size, and condition of the subject treated. By way of example, the composition may comprise between 0.005% and 10% (w/w), or 0.005% and 1% (w/w), of the active ingredient, or any fractions or multiples thereof.

Although the descriptions of pharmaceutical compositions provided herein are principally directed to pharmaceutical compositions that are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as cattle, pigs, horses, sheep, cats, and dogs.

In certain embodiments, compositions comprising at least one active ingredient are formulated using one or more pharmaceutically acceptable excipients or carriers. In other embodiments, the pharmaceutical compositions of the invention comprise a therapeutically effective amount of at least one compound of the invention and a pharmaceutically acceptable carrier. Pharmaceutically acceptable carriers, which are useful, include, but are not limited to, glycerol, water, saline, ethanol and other pharmaceutically acceptable salt solutions such as phosphates and salts of organic acids. Examples of these and other pharmaceutically acceptable carriers are described in Remington's Pharmaceutical Sciences (1991, Mack Publication Co., New Jersey).

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it may include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Multiple techniques of administering a compound exist in the art including, but not limited to: oral, nasal, inhalational, topical, buccal, rectal, pleural, peritoneal, parenteral (such as subcutaneous (s.c.), intravenous (i.v.), intramuscular (i.m.), intrasternal injection, or infusion), vaginal, transdermal, epidural, intratracheal, otic, intraocular, and intrathecal routes. In certain embodiments, the administration comprises topical administration.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. In certain embodiments, the administration comprises topical administration. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" that may be included in the pharmaceutical compositions of the invention are known in the art and described, for example in Genaro, ed. (1985, Remington's Pharmaceutical Sciences, Mack Publishing Co., Easton, Pa.), which is incorporated herein by reference.

The composition of the invention may comprise a preservative from about 0.005% to 2.0% by total weight of the composition. The preservative is used to prevent spoilage in the case of exposure to contaminants in the environment. Examples of preservatives useful in accordance with the invention included but are not limited to those selected from the group consisting of benzyl alcohol, sorbic acid, parabens, imidurea and combinations thereof. An illustrative preservative is a combination of about 0.5% to 2.0% benzyl alcohol and 0.05% to 0.5% sorbic acid.

The composition may include an antioxidant and a chelating agent that inhibit the degradation of the compound. Illustrative antioxidants are BHT, BHA, alpha-tocopherol and ascorbic acid in the range of about 0.01% to 0.3%, and/or BHT in the range of 0.03% to 0.1% by weight by total weight of the composition. The chelating agent may be present in an amount of from 0.01% to 0.5% by weight by total weight of the composition. Illustrative chelating agents include edetate salts (e.g. disodium edetate) and citric acid in the weight range of about 0.01% to 0.20% and more preferably in the range of 0.02% to 0.10% by weight by total weight of the composition. The chelating agent is useful for chelating metal ions in the composition that may be detrimental to the shelf life of the formulation. While BHT and disodium edetate are the particularly preferred antioxidant and chelating agent respectively for some compounds, other suitable and equivalent antioxidants and chelating agents may be substituted therefore as would be known to those skilled in the art.

The composition comprising an active ingredient can be administered to a mammal as frequently as several times daily, or it may be administered less frequently, such as once a day, once a week, once every two weeks, once a month, or even less frequently, such as once every several months or even once a year or less.

It is understood that the amount of compound dosed per day may be administered, in non-limiting examples, every day, every other day, every 2 days, every 3 days, every 4 days, or every 5 days. For example, with every other day administration, a 0.5-5 mg per day dose may be initiated on Monday with a first subsequent 0.5-5 mg per day dose administered on Wednesday, a second subsequent 0.5-5 mg per day dose administered on Friday, and so on. The frequency of the dose will be readily apparent to the skilled artisan and will depend upon any number of factors, such as, but not limited to, the type and severity of the disease being treated, the type and age of the animal, and so forth.

Topical Administration

An obstacle for topical administration of pharmaceuticals is the stratum corneum layer of the epidermis. The stratum corneum is a highly resistant layer comprised of protein, cholesterol, sphingolipids, free fatty acids and various other lipids, and includes cornified and living cells. One of the factors that limit the penetration rate (flux) of a compound through the stratum corneum is the amount of the active substance that can be loaded or applied onto the skin surface. The greater the amount of active substance that is applied per unit of area of the skin, the greater the concentration gradient between the skin surface and the lower layers of the skin, and in turn the greater the diffusion force of the active substance through the skin. Therefore, a formulation containing a greater concentration of the active substance is more likely to result in penetration of the active substance through the skin, and more of it, and at a more consistent rate, than a formulation having a lesser concentration, all other things being equal.

Formulations suitable for topical administration include, but are not limited to, liquid or semi-liquid preparations such as liniments, lotions, oil-in-water or water-in-oil emulsions such as creams, ointments or pastes, and solutions or suspensions. Such formulations may be applied to the skin directly or through the use of swabs, applicators, spatulas and the like, as well as in the form of transdermal patches. In certain embodiments, the patch minimizes loss of pharmaceuticals through washing, friction, scratching and/or rubbing of the skin. In other embodiments, the patch increases absorption of the pharmaceutical through the skin, while minimizing the exposure of the skin to the pharmaceutical.

Topically administrable formulations may, for example, comprise from about 0.005% to about 10% (w/w) active ingredient, although the concentration of the active ingredient may be as high as the solubility limit of the active ingredient in the solvent. Formulations for topical administration may further comprise one or more of the additional ingredients described herein.

In certain embodiments, enhancers of permeation are used to increase the rate of penetration of drugs across the skin. Typical enhancers in the art include ethanol, glycerol monolaurate, PGML (polyethylene glycol monolaurate), dimethylsulfoxide, and the like. Other enhancers include oleic acid, oleyl alcohol, ethoxydiglycol, laurocapram, alkanecarboxylic acids, dimethylsulfoxide, polar lipids, or N-methyl-2-pyrrolidone.

In certain embodiments, the compositions of the invention may contain agents that delay permeation of the active ingredient, so as to avoid acute toxicity through systemic exposure. Such agents may be combined with the sue of a patch, for example, to minimize loss of the composition from the skin.

One acceptable vehicle for topical delivery of some of the compositions of the invention may contain liposomes. The composition of the liposomes and their use are known in the art (for example, U.S. Pat. No. 6,323,219).

In certain embodiments, the pharmaceutical composition of the invention may be optionally combined with other ingredients such as adjuvants, anti-oxidants, chelating agents, surfactants, foaming agents, wetting agents, emulsifying agents, viscosifiers, buffering agents, preservatives, and the like. In other embodiments, a permeation or penetration enhancer is included in the composition and is effective in improving the percutaneous penetration of the active ingredient into and through the stratum corneum with respect to a composition lacking the permeation enhancer. Various permeation enhancers, including oleic acid, oleyl alcohol, ethoxydiglycol, laurocapram, alkanecarboxylic acids, dimethylsulfoxide, polar lipids, or N-methyl-2-pyrrolidone, are known to those of skill in the art. In another aspect, the composition may further comprise a hydrotropic agent, which functions to increase disorder in the structure of the stratum corneum, and thus allows increased transport across the stratum corneum. Various hydrotropic agents such as isopropyl alcohol, propylene glycol, or sodium xylene sulfonate, are known to those of skill in the art.

The topically active pharmaceutical composition should be applied in an amount effective to affect desired changes. As used herein, "amount effective" shall mean an amount sufficient to cover the region of skin surface where a change is desired. An active compound should be present in the amount of from about 0.0001% to about 15% by weight volume of the composition. More preferable, it should be present in an amount from about 0.0005% to about 5% of the composition; most preferably, it should be present in an amount of from about 0.005% to about 1% of the composition. Such compounds may be synthetically- or naturally derived.

Controlled Release Formulations and Drug Delivery Systems

Controlled- or sustained-release formulations of a pharmaceutical composition of the invention may be made using conventional technology. In some cases, the dosage forms to be used can be provided as slow or controlled-release of one or more active ingredients therein using, for example, hydropropylmethyl cellulose, other polymer matrices, gels, permeable membranes, osmotic systems, multilayer coatings, microparticles, liposomes, or microspheres or a combination thereof to provide the desired release profile in varying proportions. Suitable controlled-release formulations known to those of ordinary skill in the art, including those described herein, can be readily selected for use with the pharmaceutical compositions of the invention. Thus, single unit dosage forms suitable for topical administration, such as liniments, lotions, oil-in-water or water-in-oil emulsions such as creams, ointments or pastes, transdermal patches, and solutions or suspensions that are adapted for controlled-release are encompassed by the present invention.

Most controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood level of the drug, and thus can affect the occurrence of side effects.

Most controlled-release formulations are designed to initially release an amount of drug that promptly produces the desired therapeutic effect, and gradually and continually release of other amounts of drug to maintain this level of therapeutic effect over an extended period of time. In order to maintain this constant level of drug in the body, the drug must be released from the dosage form at a rate that will replace the amount of drug being metabolized and excreted from the body.

Controlled-release of an active ingredient can be stimulated by various inducers, for example pH, temperature, enzymes, water, or other physiological conditions or compounds. The term "controlled-release component" in the context of the present invention is defined herein as a compound or compounds, including, but not limited to, polymers, polymer matrices, gels, permeable membranes, liposomes, or microspheres or a combination thereof that facilitates the controlled-release of the active ingredient.

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release that is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In certain embodiments of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.
Materials and Methods Unless otherwise noted, all cell lines, starting materials and resins were obtained from commercial suppliers and used without purification.

Example 1: Effects of Vitamin $D_3$ Analog MC903

Figure 2:
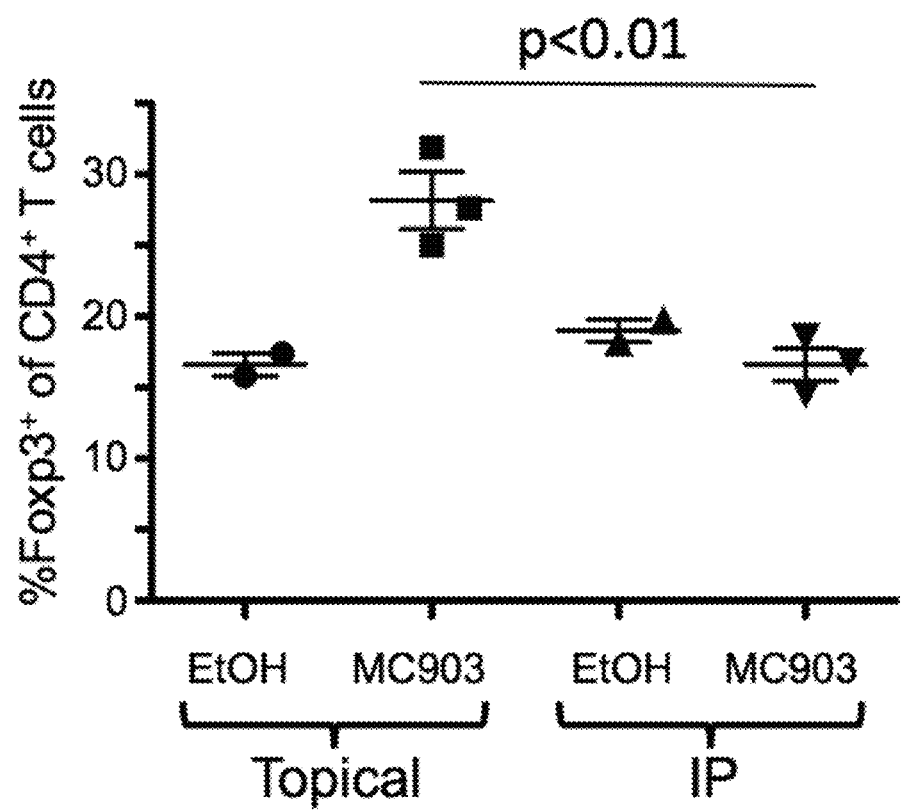
FIG. 2 is a graph illustrating the percentage of Tregs out of CD4+ T cells in the spleen after B6 mice were treated topically or injected intraperitoneally with EtOH or MC903 (2 nmol).

Wildtype (WT) mice were treated with vehicle (100% EtOH) or MC903 once a day on the skin of one ear for 7 days. On Day 8, the ear skin of both ears, blood, and secondary lymphoid organs (lymph nodes and spleen) were harvested. Compared to the EtOH-treated (MC903-untreated) side, the MC903-treated ear skin showed a significant increase (about 2 fold) in the fraction of Tregs (% Foxp3+ of CD4+ T cells; FIG. 1A). Similar increases were seen systemically in the blood and in all secondary lymphoid organs tested (FIG. 1B). No effect was observed when MC903 was injected intraperitoneally, suggesting that the effect was mediated by the skin (FIG. 2).

Figure 3A:
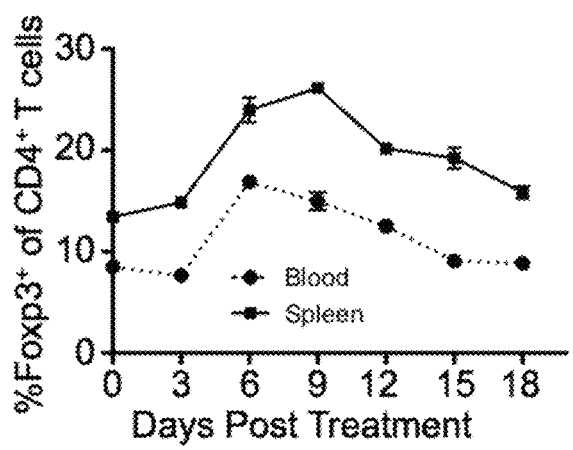
FIG. 3A-3C comprise graphs illustrating data derived from topical treatment of B6 mice with EtOH or MC903 (2 nmol) until Day 6. Mice were taken at different time points post treatment initiation as indicated.
Figure 3B:
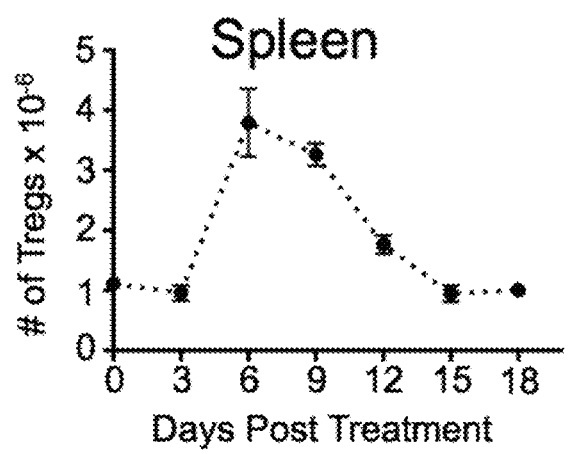
Figure 3C:
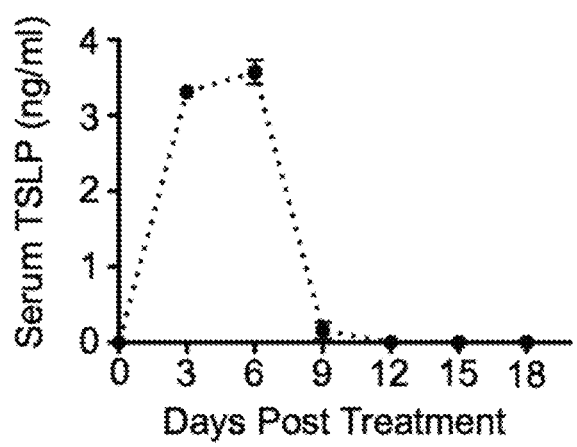
Figure 4A:
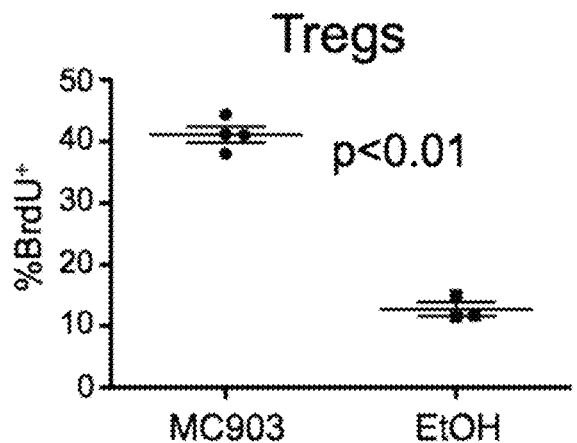
FIGS. 4A-4B comprise graphs illustrating data derived from topical treatment of B6 mice with EtOH or MC903 (2 nmol) daily and BrdU (intraperitoneal injection as a loading dose, followed by administration of drinking water) for the last 3 days.
Figure 4B:
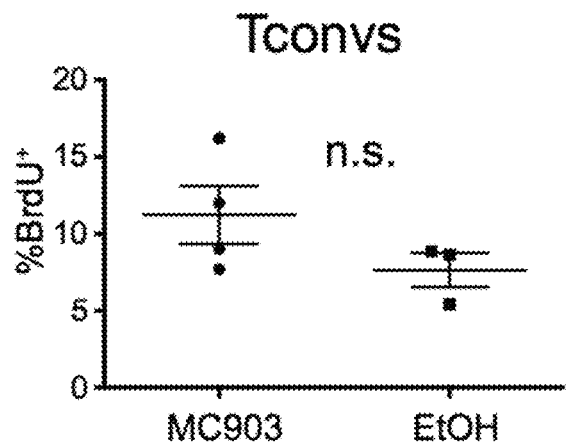

Next, the kinetics of the systemic increase in Treg levels was investigated after topical MC903 treatment (treatment stopped on Day 7). The absolute number and the fraction of Tregs increased to a peak between days 6 and 9 and gradually declined thereafter in the spleen and the blood of MC903-treated mice (FIGS. 3A-3B). Circulating TSLP levels peaked at Day 6 and fell abruptly by Day 9 (FIG. 3C). By Day 15, no differences in Treg levels were seen between the EtOH and MC903-treated groups, suggesting that the effect of MC903 was reversible after cessation of treatment. The increase in Treg levels was associated with enhanced BrdU incorporation by Tregs suggesting that the proliferation of Tregs was increased (FIG. 4A). In contrast, no significant increase in BrdU incorporation by conventional CD4+ T cells (Tconvs) was seen (FIG. 4B), suggesting that there was a selective effect of MC903 on Treg proliferation.

Example 2: Topical MC903 Application Decreases the Incidence of T1D in NOD Mice

Figure 5A:
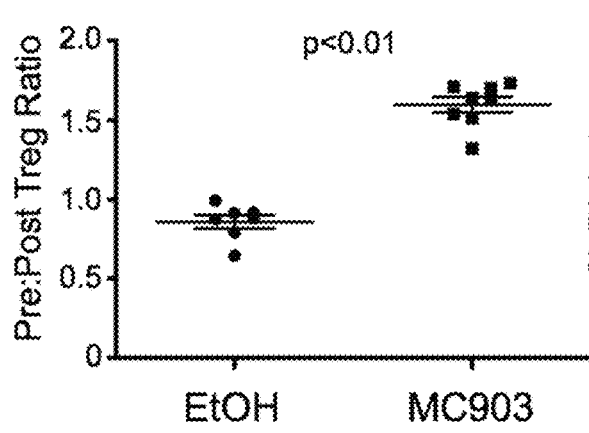
FIGS. 5A-5B comprise graphs illustrating data derived from topical treatment of NOD mice with EtOH or MC903 (2 nmol) 3 times/week every other week at Week 5 of age; treatment was stopped at Week 15 of age.
Figure 5B:
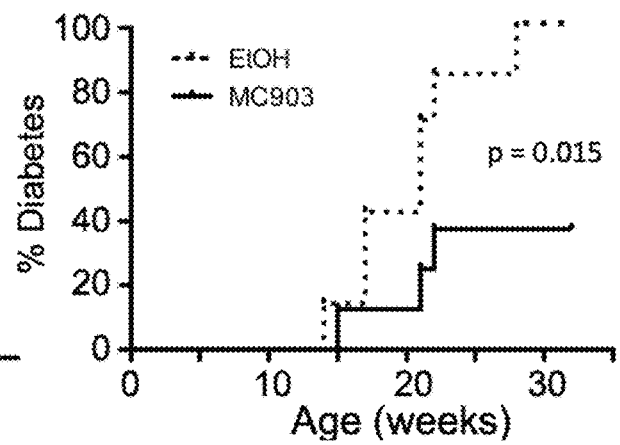

To test whether topical treatment with MC903 would lead to amerilioration of inflammatory disorders, it was tested whether topical application of MC903 protected a mouse against type I diabetes (T1D), using a non-obese diabetes (NOD) mouse model of diabetes. NOD mice were treated 3 times a week with MC903 on alternating ears every week. This treatment protocol allowed to continue MC903 treatment for 8 weeks with little to no evidence of atopic dermatitis. NOD mice receiving this treatment displayed increased circulating Treg levels at Day 8 post-treatment with MC903 compared to vehicle (FIG. 5A). Importantly, the incidence of T1D as determined by two consecutive readings of a spot blood glucose level of >250 mg/dl was significantly attenuated in mice treated with topical MC903 compared to vehicle (FIG. 5B).

Figure 6A:
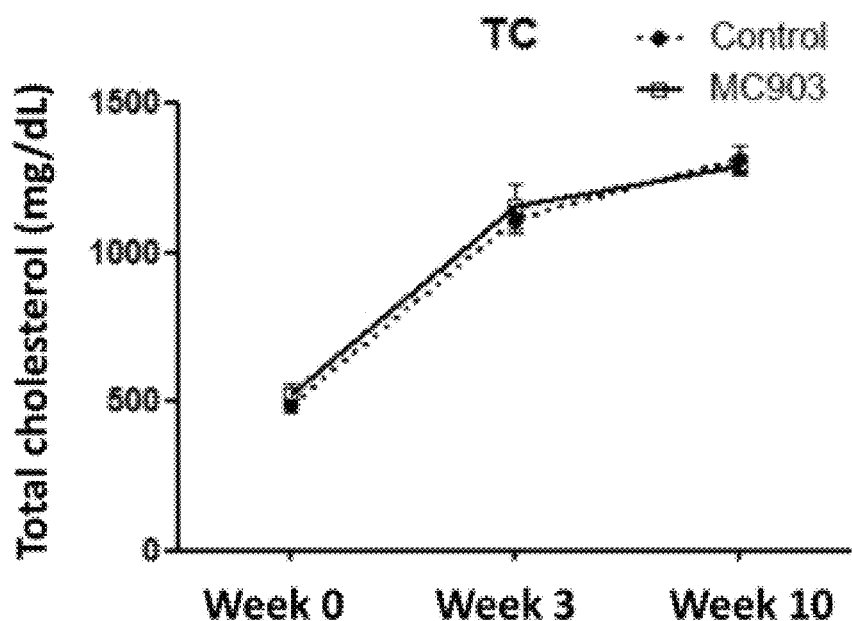
FIGS. 6A-6B comprise graphs illustrating data derived from topical treatment of ApoE KO mice fed a high-fat Western diet with EtOH or MC903 (2 nmol) 3 times/week every other week for 10 weeks.
Figure 6B:
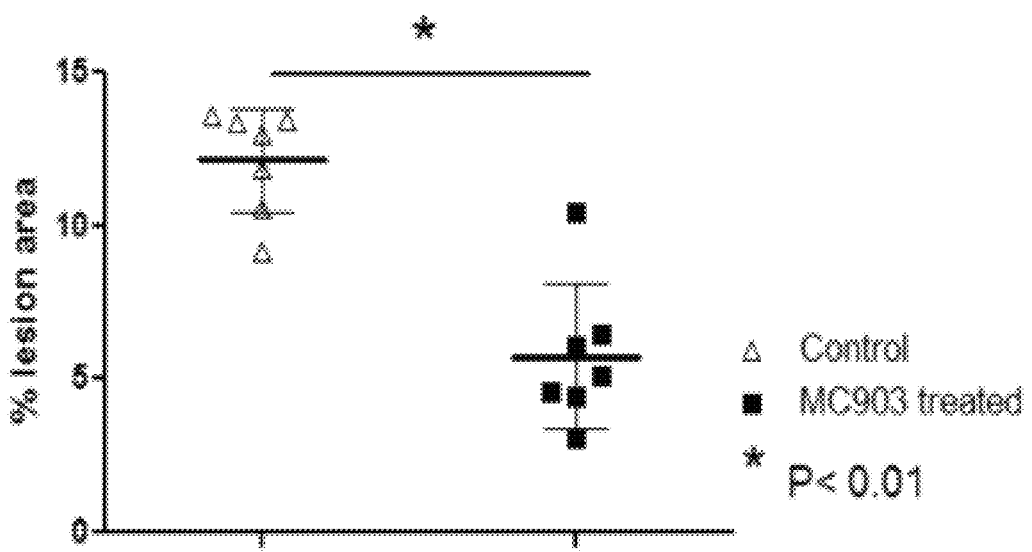

Example 3: Topical MC903 Application Decreases Atherosclerotic Lesion Size in ApoE KO Mice The effects of topical application of MC903 on atherosclerotic plaques were investigated. Atherosclerosis is a disease condition where lipid deposition occurs in arterial walls, leading to obstruction of blood flow. Ultimately, these lesions cause morbidity and mortality by affecting blood flow to the heart (myocardial infarction; angina) or the brain (stroke). Although these lesions are formed by cholesterol deposits in patients who have hypercholesterolemia, immune activation is necessary for plaque progression, and Tregs are implicated in dampening the progression of atherosclerosis. It is contemplated that topical MC903 treatment can attenuate plaque progression in atherosclerosis. To test this hypothesis, the ApoE KO mouse model of atherosclerosis was used. ApoE KO mice fed with a high fat Western diet were treated topically with MC903 every other day (3 times week) on every other week for 10 weeks. Although treatment with MC903 did not alter total cholesterol levels in ApoE KO mice (FIG. 6A), the % of area occupied by the plaques in the aorta was significantly decreased by >50% (FIG. 6B). These data suggest that topical MC903 treatment may be effective in reducing atherosclerotic plaque progression in hypercholesterolemia patients.

Example 4: Topical MC903 Application Decreases EAE Severity in Mice

Figure 7:
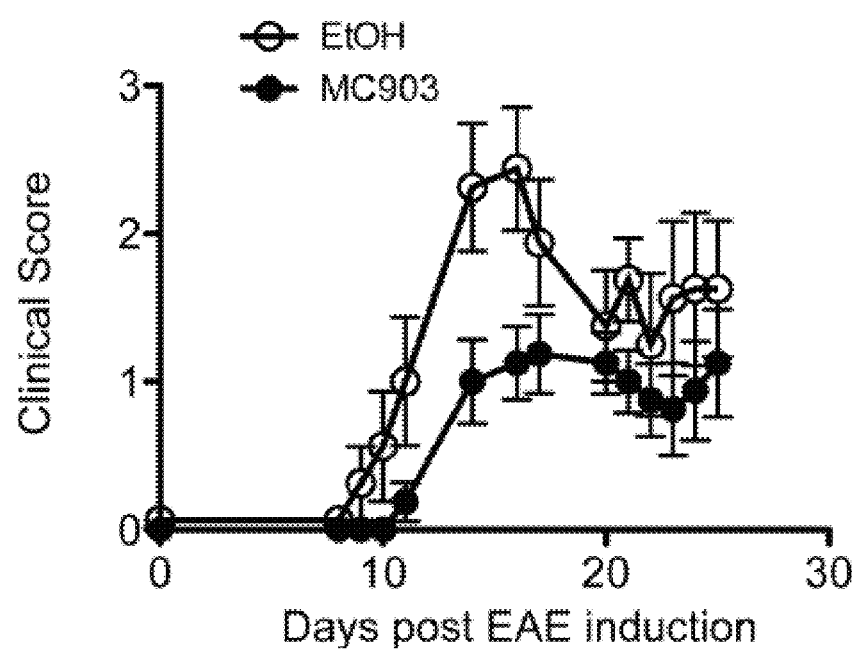
FIG. 7 illustrates the clinical score difference among B6 mice topically treated with EtOH or MC903 daily for 2 weeks. The B6 mice were injected with myelin oligodendrocyte glycoprotein (MOG) peptide emulsified in complete Freund's adjuvant (CFA), then received Pertussis toxin intraperitoneally at the time of immunization and 48 h later. The mice were treated with topical EtOH or MC903 daily for 2 weeks. Mice were clinically scored on a five-point scale for signs of disease on the indicated days. N=8 mice/group. P=0.06 by two-way Analysis of variance (ANOVA).

To test whether topical MC903 treatment was effective at treating multiple sclerosis (MS), the effect of MC903 in reducing clinical severity of a mouse model of MS known as experimental allergic encephalitis (EAE). Mice were topically treated daily with MC903 starting 1 day before disease induction. Topical MC903 treatment resulted in attenuated clinical severity compared to EtOH-treated mice (FIG. 7).

Thus, topical MC903 treatment might also be beneficial in the treatment of multiple sclerosis.

Figure 8A:
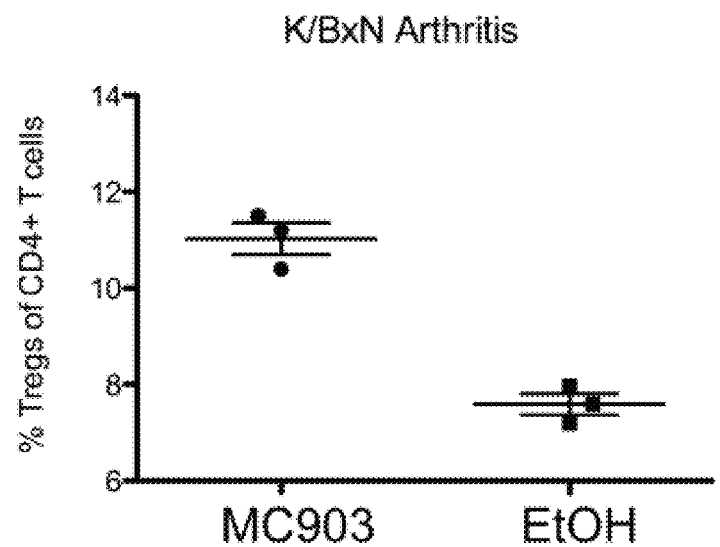
FIGS. 8A-8B comprise graphs illustrating data derived from injecting B6 mice with 75 µl of serum from K/B×N mice on Days 0 and 2, and topically treating the mice with MC903 starting at Day 0.
Figure 8B:
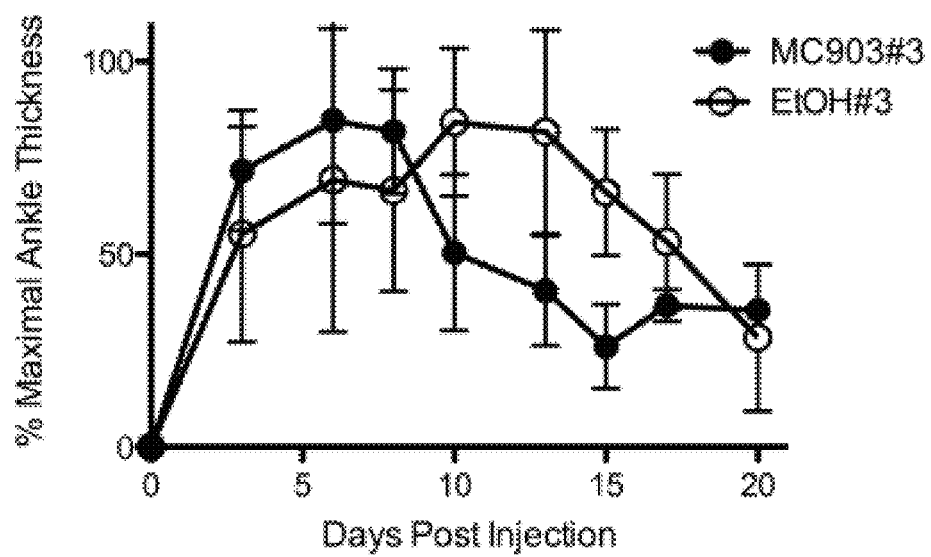

Example 5: Topical MC903 Application Decreases Swelling and Erythema in Serum-Induced Arthritis Whether MC903 treatment can attenuate joint swelling in a mouse model of rheumatoid arthritis was tested in the following experiment. In this model, serum from arthritic mice (K/BxN) is injected into normal wildtype mice. This results in joint swelling ~3-5 days later with resolution in ~2-3 weeks. Mice were treated topically with MC903 or EtOH (daily) and injected with arthritogenic serum (on Days 0 and 2). Similar to unmanipulated wildtype mice, MC903 treatment increased circulating Treg levels in mice injected with arithrotogenic serum (FIG. 8A). Although joint swelling was similar between both groups until Day 7 post MC903 treatment, a quick reduction in joint swelling and erythema was seen concomitant with the elevated Treg percentages (FIG. 8B). These data suggest that MC903 treatment can reduce joint swelling associated with rheumatoid arthritis.

Figure 9A:
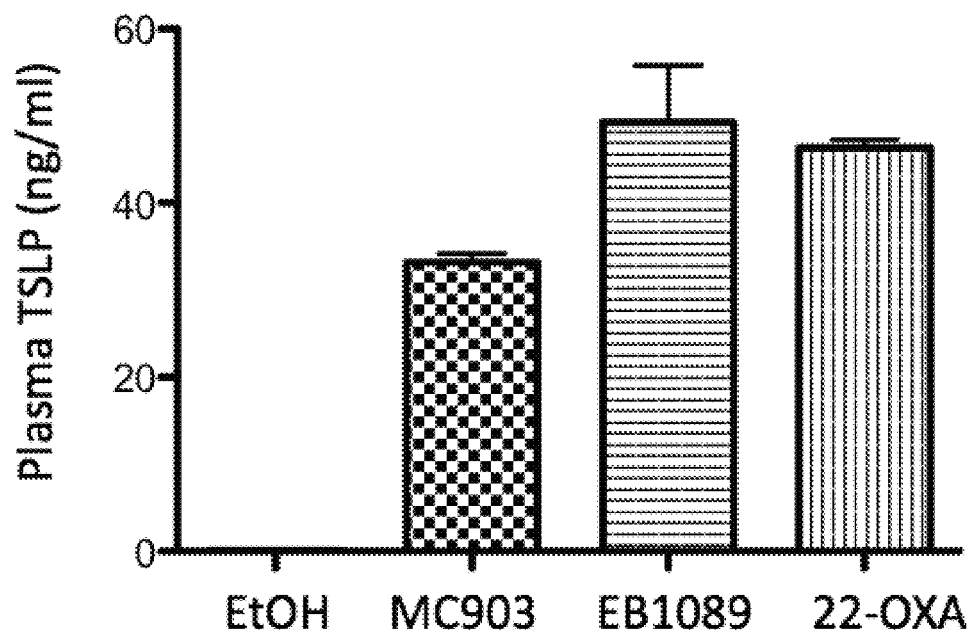
FIGS. 9A-9C comprise bar graphs illustrating data derived from topically treating mice with EtOH, MC903, EB1089, or 22-OXA for 4 days and bleeding them on Day 5.
Figure 9B:
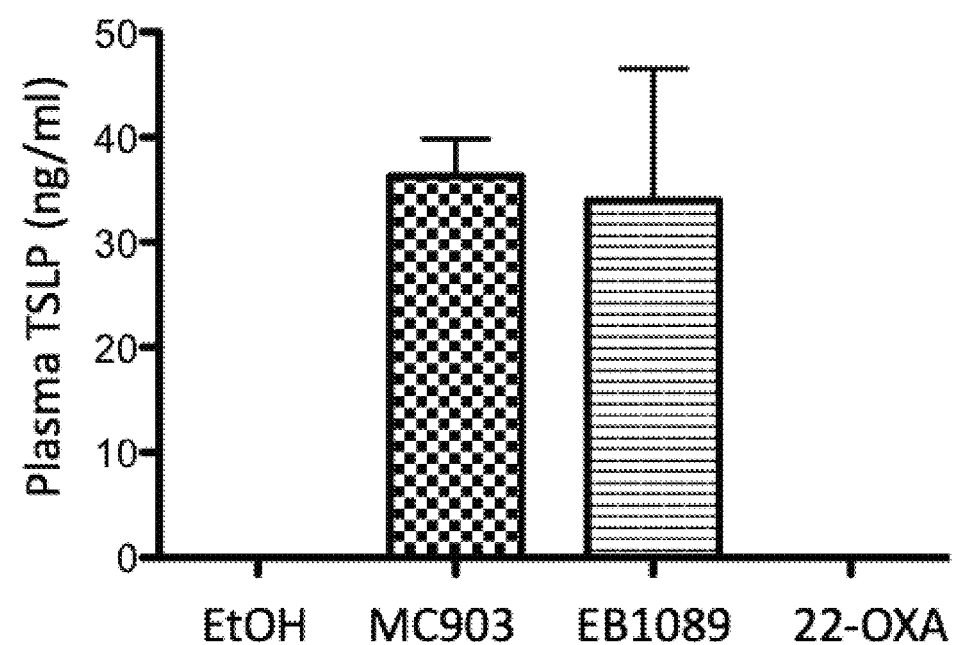
Figure 9C:
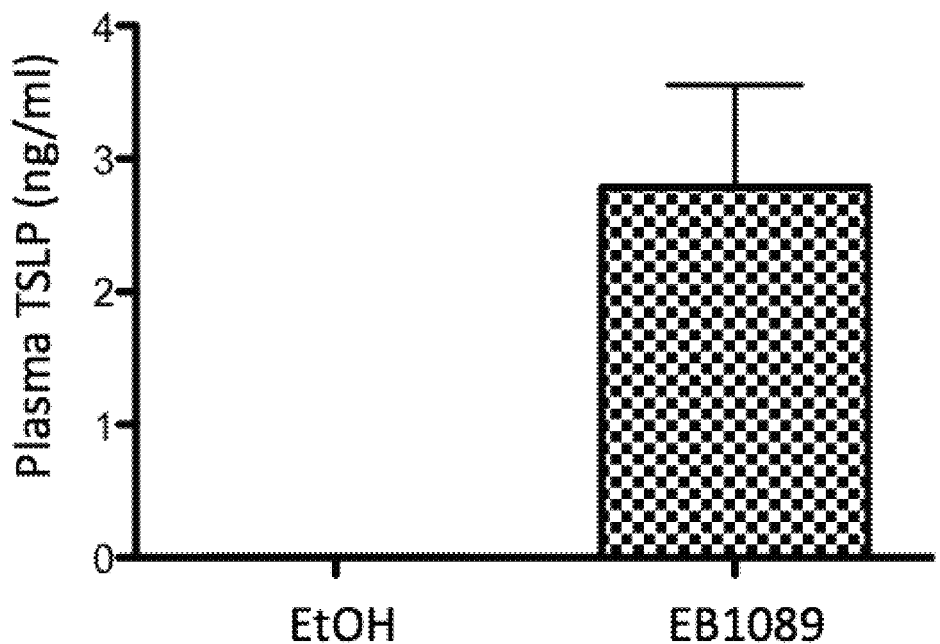
Figure 10A:
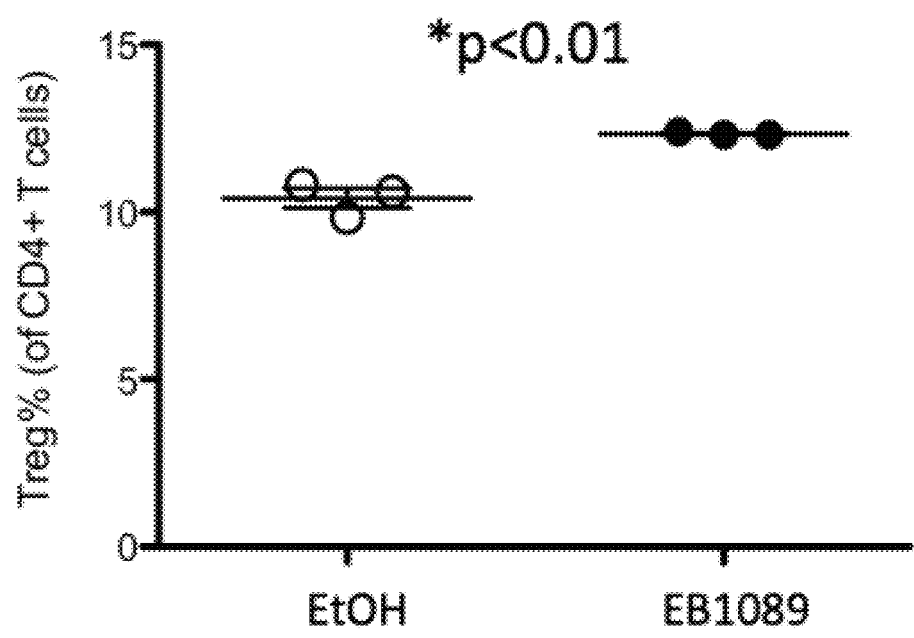
FIGS. 10A-10B comprise bar graphs illustrating data derived from topically treating mice with EtOH or EB1089 (0.04 nmol/ear) for 5 days and bleeding them on Day 7. Treg % from (FIG. 10A) blood and (FIG. 10B) spleen are illustrated. N=3 mice/group. *p<0.01 by Student t-test.
Figure 10B:
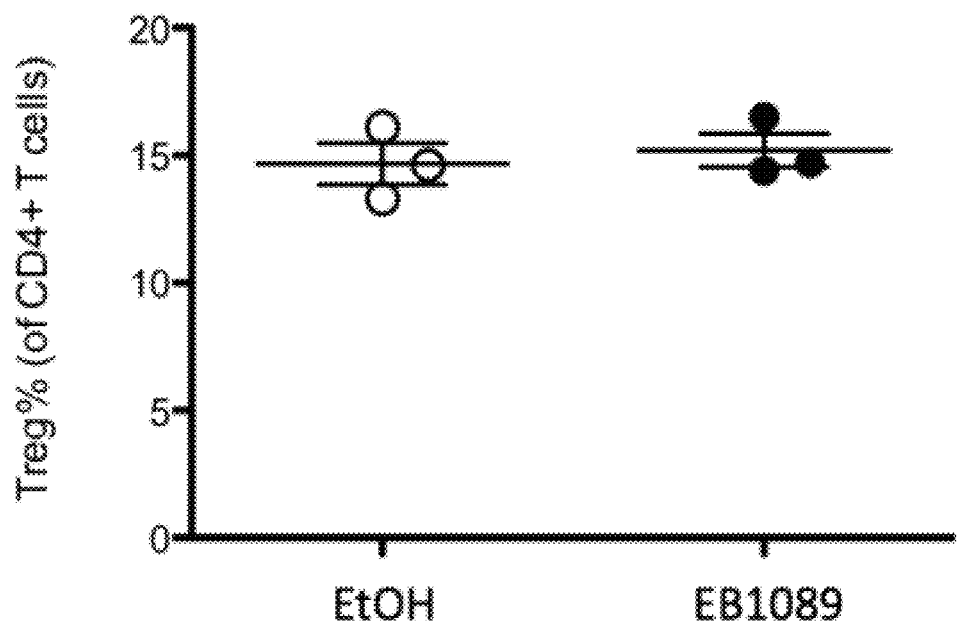

Example 6: Investigation of Various Vitamin $D_3$ Analogs in Systemic TSLP Induction VDR stimulation of keratinocytes led to TSLP production, which in certain embodiments caused increase in Treg numbers. The effects of two vitamin $D_3$ analogs (22-Oxacalcitriol, also known as 22-OXA, and EB1089) on TSLP production and Treg numbers were evaluated. Similarly to MC903, 22-OXA and EB1089 were applied to the ear skin bilaterally at a dose of 2 nmol/ear dissolved in ethanol. After 5 days of treatment, the mice were bled and serum TSLP levels were measured. Both 22-OXA and EB1089 induced detectable amounts of TSLP, comparable to what was seen with MC903 topical treatment (FIG. 9A). However, the effect of the topical treatment on Tregs could not be assessed due to toxicity-related morbidity and mortality of mice treated with 22-OXA or EB1089. To avoid the toxic effect, the dose of 22-OXA and EB1089 was lowered to a point where morbidity and mortality of mice was not observed (0.4 nmol/ear for 22-OXA; 0.04 nmol/ear for EB1089). At this dose, no increase in TSLP level was detected in 22-OXA-treated mice (FIG. 9B). Although some TSLP was detectable for EB1089 at 0.04 nmol/ear (FIG. 9C), only a subtle increase in blood Tregs was observed at this dose (FIG. 10A). Moreover, EB1089 (0.04 nmol/ear) did not have any effect on splenic Treg numbers (FIG. 10B). These data indicate that these two vitamin $D_3$ analogs do not exhibit the desired effect. In comparison, MC903 can induce TSLP production and increase systemic Treg numbers without any apparent systemic toxicity.

In certain embodiments, a vitamin $D_3$ analog induces TSLP from keratinocytes (as demonstrated herein for 22-OXA and EB1089, for example). Without wishing to be limited by any theory, toxicity of a vitamin $D_3$ analog is minimized if it has low bioavailability (limited skin penetration). Without wishing to be limited by any theory, toxicity of a vitamin $D_3$ analog is minimized if it binds poorly or does not bind significantly to the vitamin D binding protein. In certain embodiments, poor or insignificant association of a vitamin $D_3$ analog with vitamin D binding protein ensures rapid excretion of the analog from systemic circulation, minimizing systemic toxicity. In other embodiments, MC903 has low skin bioavailability (limited skin penetration). In yet other embodiments, MC903 binds poorly or does not bind significantly to the vitamin D binding protein Example 7: Dosing Schedule of MC903 for Long-Term Use and Sustained Increase in Systemic Treg Numbers As demonstrated elsewhere herein, topical MC903 treatment leads to sustained increases in systemic Treg numbers, which is beneficial in treating inflammatory disorders. To test whether chronic MC903 treatment results in sustained increases in Treg numbers, mice were continuously treated with MC903 for more than 2 weeks.

Figure 11:
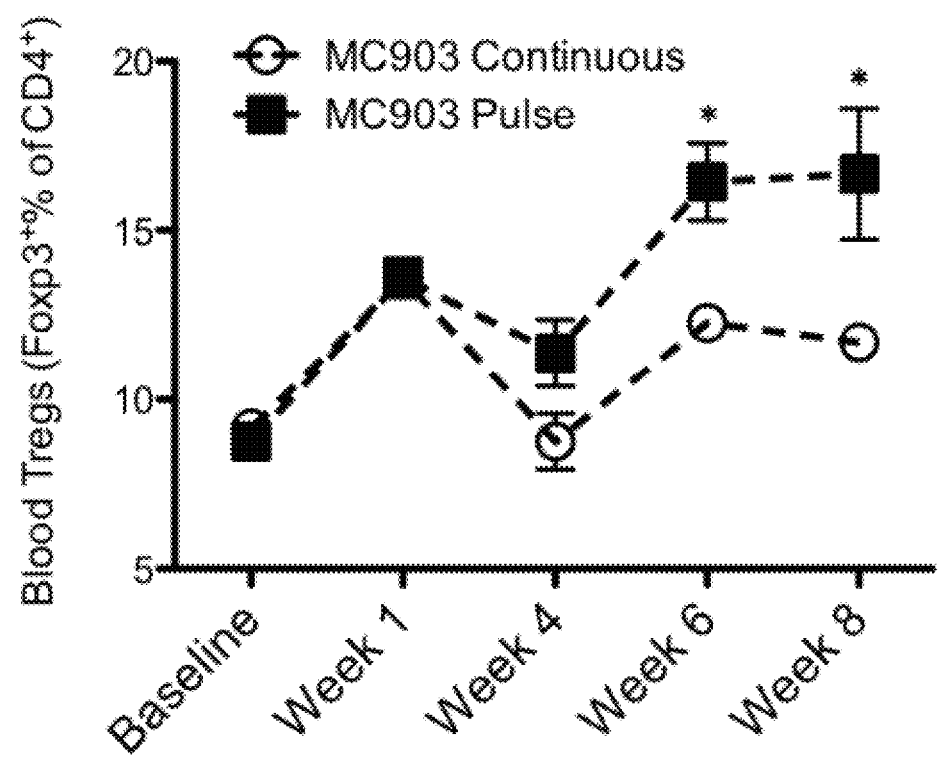
FIG. 11 comprises a graph illustrating data derived from topically treating mice with MC903 (2 nmol on one ear) 3 times/week every other week or with MC903 (2 nmol on one ear) 3 times/week every week (alternating ears every week) for 8 weeks. The % of Tregs out of CD4+ T cells in the blood before (baseline) and after treatment (Weeks 1, 4, 6, and 8) is illustrated. N=3 mice/group. *p<0.05 by Student t-test.
Figure 12:
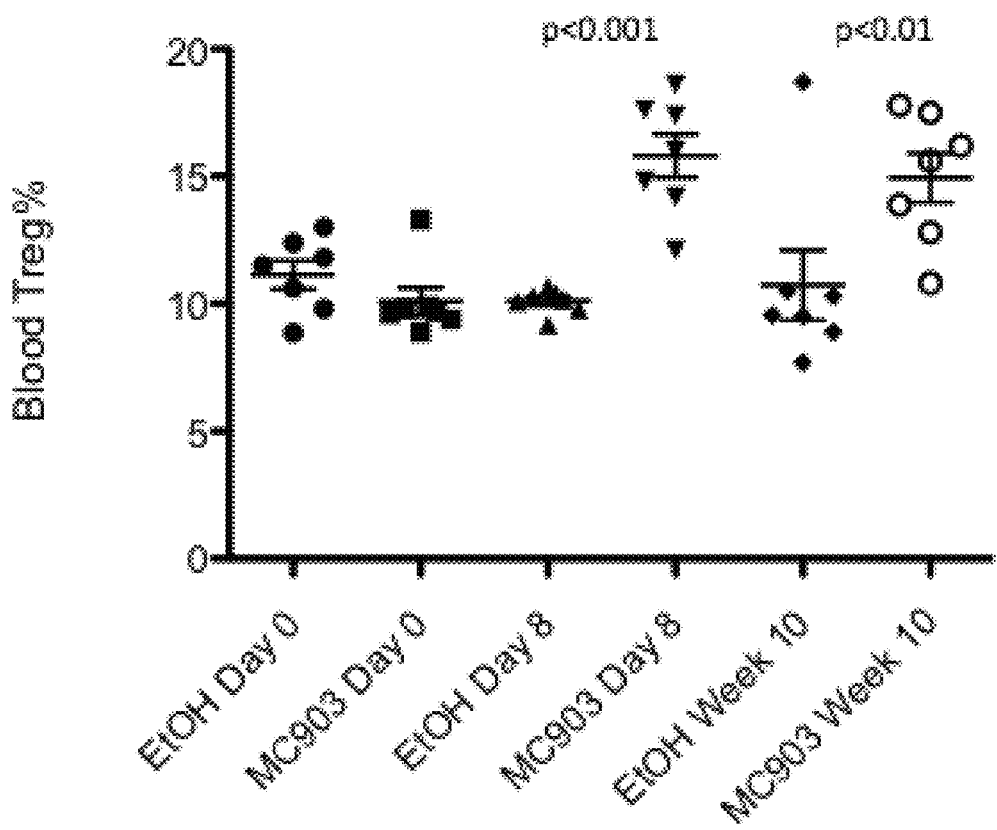
FIG. 12 comprises a graph illustrating data derived from topically treating mice with EtOH or MC903 (2 nmol) 3 times/week every other week for 10 weeks. The % of Tregs out of CD4+ T cells in the blood before (Day 0) and after treatment (Day 8 and Week 10) is illustrated. N=7 mice/group.

Chronic MC903 treatment (once/day) of more than 1 week led to the development of atopic dermatitis of the ear skin, which made it impossible to continue with the treatment. To avoid this local toxic effect of MC903, alternating ears were treated every week (right ear for 1 week, followed by the left ear for 1 week, then back to the right ear for 1 week, and so on). This allowed for chronic treatment with MC903 with minimal atopic dermatitis. Using this alternating ear protocol, although Tregs were increased systemically at Day 8 as expected, circulating Tregs were not increased at Week 4 of treatment and beyond (FIG. 11). Without wishing to be limited by any theory, the increase in Tregs appeared to be become refractory to the chronic MC903 treatment. Thus, the protocol was modified so that a 1-week rest period (pulse treatment) was given between weekly treatments. When mice were treated with MC903 for 3 days (every other day)/week every other week (one week of treatment and one week of rest), atopic inflammation was avoided and the increase in circulating Treg numbers was increased over a 10 week period (FIGS. 11-12).

In certain embodiments, the dosing schedule of chronic MC903 application for the treatment of inflammatory disease comprises weekly treatment (every day or every other day; minimum of 3 days/week) with at least a week of no treatment, which can be cycled as a dosing schedule. In other embodiments, the dose of MC903 to be used ranges from about 0.2 nmol to about 20 nmol per $cm^2$ of skin treated. In yet other embodiments, the skin area treated ranges from about 100 $cm^2$ to 2,500 $cm^2$ for the effect to be achieved.

Figure 13:
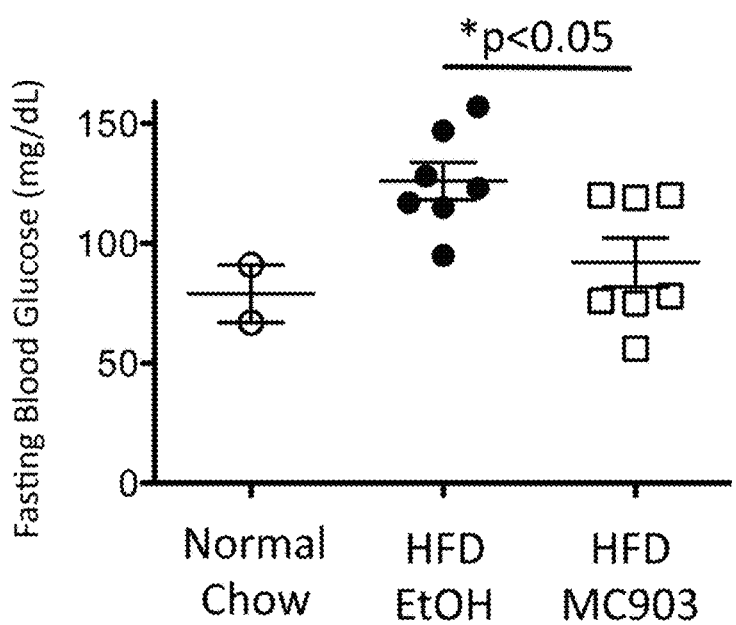
FIG. 13 comprises a graph illustrating the finding that topical administration of MC903 improves overnight fasting glucose levels in mice fed with 12 weeks of high fat diet (HFD).
Figure 14:
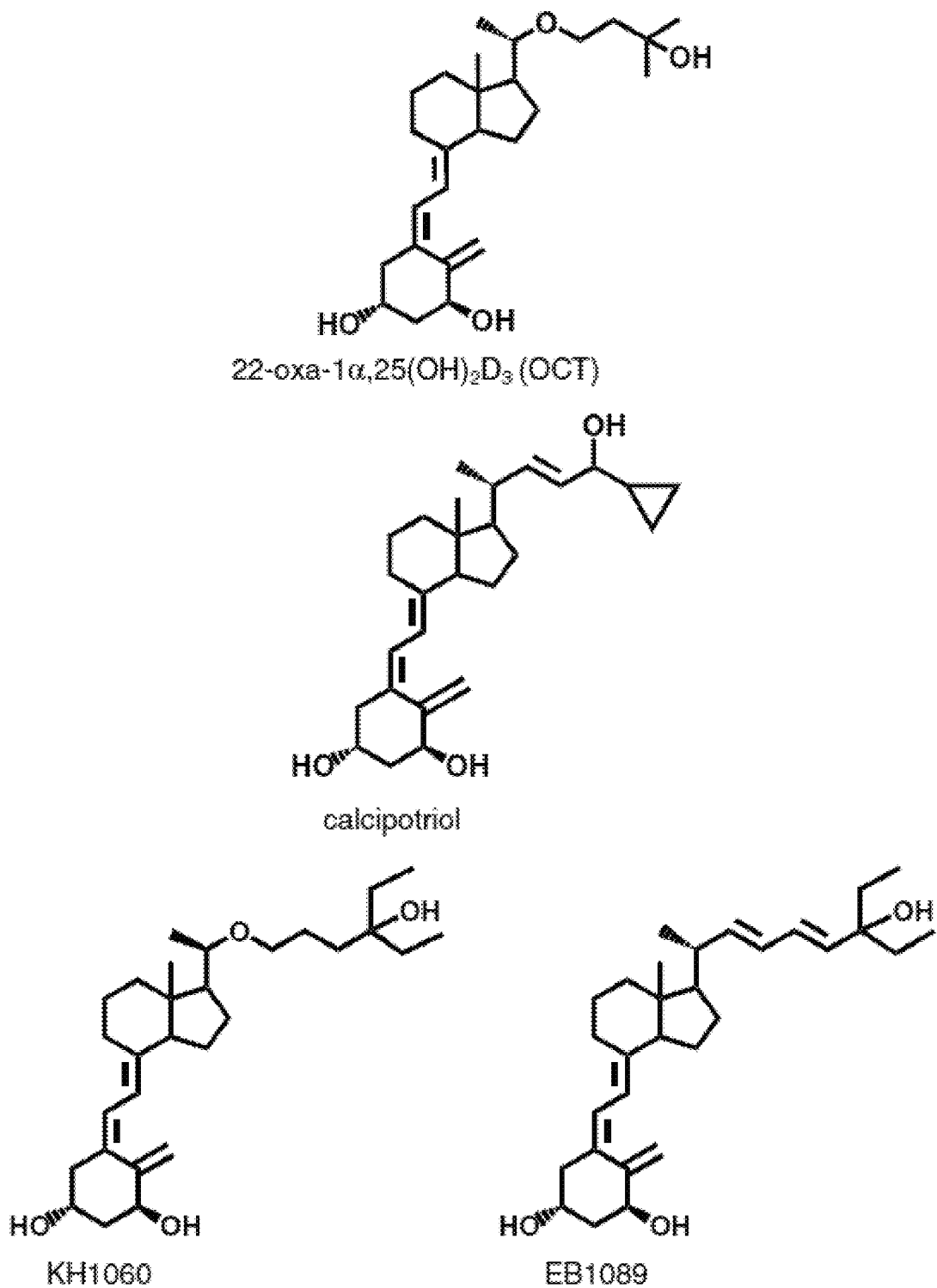
FIG. 14 illustrates certain vitamin $D_3$ analogs contemplated within the invention.

Example 8: Topical MC903 Application Improves Overnight Fasting Glucose Levels in Mice on a High Fat Diet Topical administration of MC903 was evaluated in a model of high fat diet (HFD) type II diabetes mice. Male C57BL6 mice, which were 8 weeks at the onset of the study, were used. The mice were fed a high fat diet (45 kcal % of fat; research diet No. D12451, OpenSource Diets) for 20 weeks. During this period, the mice were topically administered ethanol or MC903 three times a week (Monday, Wednesday and Friday), every other week, for the duration of the experiment. As illustrated in FIG. 13, those mice treated with MC903 demonstrated improved overnight fasting glucose levels, suggesting that topical treatment with MC903 may help treat type II diabetes in mammals.

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of promoting proliferation of systemic peripheral regulatory T cells (Tregs) in a subject in need thereof, the method comprising:
   administering to the subject a pharmaceutically effective amount of a polypeptide comprising a thymic stromal lymphopoietin (TSLP) isoform,
   wherein proliferation of systemic peripheral Tregs is promoted in the subject,
   wherein the isoform has at least 85% identity with at least one selected from the group consisting of SEQ ID NO:1 and SEQ ID NO:2.

2. The method of claim 1, wherein the TSLP isoform is at least one selected from the group consisting of SEQ ID NO:1 and SEQ ID NO:2.

3. The method of claim 1, wherein the subject is human.

4. The method of claim 1, wherein the TSLP isoform has at least 90% identity with at least one selected from the group consisting of SEQ ID NO:1 and SEQ ID NO:2.

5. The method of claim 1, wherein the TSLP isoform has at least 95% identity with at least one selected from the group consisting of SEQ ID NO:1 and SEQ ID NO:2.

6. The method of claim 1, wherein the TSLP isoform has at least 99% identity with at least one selected from the group consisting of SEQ ID NO:1 and SEQ ID NO:2.

\* \* \* \* \*

SEQUENCE LISTING

```
<160> NUMBER OF SEQ ID NOS: 2

<210> SEQ ID NO 1
<211> LENGTH: 159
<212> TYPE: PRT
<213> ORGANISM: Artificial Sequence
<220> FEATURE:
<223> OTHER INFORMATION: Chemically synthesized

<400> SEQUENCE: 1

Met Phe Pro Phe Ala Leu Leu Tyr Val Leu Ser Val Ser Phe Arg Lys
1               5                   10                  15

Ile Phe Ile Leu Gln Leu Val Gly Leu Val Leu Thr Tyr Asp Phe Thr
            20                  25                  30

Asn Cys Asp Phe Glu Lys Ile Lys Ala Ala Tyr Leu Ser Thr Ile Ser
        35                  40                  45

Lys Asp Leu Ile Thr Tyr Met Ser Gly Thr Lys Ser Thr Glu Phe Asn
    50                  55                  60

Asn Thr Val Ser Cys Ser Asn Arg Pro His Cys Leu Thr Glu Ile Gln
65                  70                  75                  80

Ser Leu Thr Phe Asn Pro Thr Ala Gly Cys Ala Ser Leu Ala Lys Glu
                85                  90                  95

Met Phe Ala Met Lys Thr Lys Ala Ala Leu Ala Ile Trp Cys Pro Gly
            100                 105                 110

Tyr Ser Glu Thr Gln Ile Asn Ala Thr Gln Ala Met Lys Lys Arg Arg
        115                 120                 125

Lys Arg Lys Val Thr Thr Asn Lys Cys Leu Glu Gln Val Ser Gln Leu
    130                 135                 140

Gln Gly Leu Trp Arg Arg Phe Asn Arg Pro Leu Leu Lys Gln Gln
145                 150                 155

<210> SEQ ID NO 2
<211> LENGTH: 63
<212> TYPE: PRT
<213> ORGANISM: Artificial Sequence
<220> FEATURE:
<223> OTHER INFORMATION: Chemically synthesized

<400> SEQUENCE: 2

Met Phe Ala Met Lys Thr Lys Ala Ala Leu Ala Ile Trp Cys Pro Gly
1               5                   10                  15

Tyr Ser Glu Thr Gln Ile Asn Ala Thr Gln Ala Met Lys Lys Arg Arg
            20                  25                  30

Lys Arg Lys Val Thr Thr Asn Lys Cys Leu Glu Gln Val Ser Gln Leu
        35                  40                  45

Gln Gly Leu Trp Arg Arg Phe Asn Arg Pro Leu Leu Lys Gln Gln
    50                  55                  60
```